United States Patent
Middleton (12) 
(10) Patent No.: US 6,656,224 B2
(45) Date of Patent: *Dec. 2, 2003

(54) ARTIFICIAL INTERVERTEBRAL DISC

(75) Inventor: Lance M. Middleton, Trumbull, CT (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/921,876

(22) Filed: Aug. 3, 2001

(65) Prior Publication Data

US 2001/0051829 A1 Dec. 13, 2001

Related U.S. Application Data

(62) Division of application No. 09/098,606, filed on Jun. 17, 1998, now Pat. No. 6,296,664.

(51) Int. Cl.$^7$ .................................................. A61F 2/44
(52) U.S. Cl. .................................................. 623/17.16
(58) Field of Search ........................... 623/17.15, 17.13, 623/17.16, 17.11

(56) References Cited

U.S. PATENT DOCUMENTS

| | | |
|---|---|---|
| 4,309,777 A | 1/1982 | Patil |
| 4,349,921 A | 9/1982 | Kuntz |
| 4,714,469 A | 12/1987 | Kenna |
| 4,759,769 A | 7/1988 | Hedman et al. |
| 4,863,477 A | 9/1989 | Monson |
| 4,874,389 A | 10/1989 | Downey |
| 4,911,718 A | 3/1990 | Lee et al. |
| 4,932,975 A | 6/1990 | Main et al. |
| 4,997,432 A | 3/1991 | Keller |
| 5,035,716 A | 7/1991 | Downey |
| 5,108,438 A | 4/1992 | Stone |

(List continued on next page.)

FOREIGN PATENT DOCUMENTS

| | | |
|---|---|---|
| DE | P 36 20 549 | 6/1986 |
| DE | 41 09 941 | 10/1991 |
| DE | 42 20 218 | 12/1993 |
| EP | 0 346 269 | 6/1989 |
| FR | 2124815 | 9/1972 |
| RU | 2 004 218 | 2/1991 |
| WO | WO 87/07827 | 12/1987 |
| WO | WO 94/23671 | 10/1994 |

Primary Examiner—Bruce Snow
(74) Attorney, Agent, or Firm—Lerner, David, Littenberg, Krumholz & Mentlik, LLP (57) ABSTRACT

An intervertebral prosthesis includes a disc member dimensioned for insertion within an intervertebral space between adjacent vertebrae to replace at least a portion of an intervertebral disc removed therefrom. The disc member has sufficient rigidity to support the adjacent vertebrae in spaced relation, and defines a longitudinal axis extending the height of the disc member and a lateral axis transverse to the longitudinal axis. The disc member includes an exterior wall which has a slit defined therein. The slit defines a longitudinal component of direction and a lateral component of direction. Preferably, the exterior wall includes a plurality of helical slits, adjacent slits being disposed in at least partial overlapping relation to define an overlapping region. Upon insertion of the disc member within the intervertebral space with the support surfaces in contacting engagement with respective vertebral portions of the adjacent vertebrae, forces exerted by the vertebral portions on the support surfaces are transferred along the exterior wall through the overlapping region.

5 Claims, 7 Drawing Sheets

U.S. PATENT DOCUMENTS

| | | |
|---|---|---|
| 5,123,926 A | 6/1992 | Pisharodi |
| 5,147,404 A | 9/1992 | Downey |
| 5,171,278 A | 12/1992 | Pisharodi |
| 5,171,280 A | 12/1992 | Baumgartner |
| 5,171,281 A | 12/1992 | Parsons et al. |
| 5,192,327 A | 3/1993 | Brantigan |
| 5,258,031 A | 11/1993 | Salib et al. |
| 5,306,308 A | 4/1994 | Gross et al. |
| 5,306,309 A | 4/1994 | Wagner et al. |
| 5,306,310 A * | 4/1994 | Siebels ............... 623/17 |
| 5,314,478 A | 5/1994 | Oka et al. |
| 5,320,644 A | 6/1994 | Baumgartner |
| 5,423,816 A | 6/1995 | Lin |
| 5,423,817 A | 6/1995 | Lin |
| 5,458,638 A | 10/1995 | Kuslich et al. |
| 5,458,642 A | 10/1995 | Beer et al. |
| 5,507,016 A | 4/1996 | Okuhara |
| 5,514,180 A | 5/1996 | Heggeness et al. |
| 5,645,598 A | 7/1997 | Brosnahan, III |
| 5,674,294 A | 10/1997 | Bainville et al. |
| 5,676,702 A | 10/1997 | Ratron |
| 5,702,449 A | 12/1997 | McKay |
| 5,702,450 A | 12/1997 | Bisserie |
| 5,755,798 A | 5/1998 | Papavero et al. |
| 5,824,094 A | 10/1998 | Serhan et al. |
| 5,888,227 A | 3/1999 | Cottle |
| 6,086,613 A * | 7/2000 | Camino et al. ............ 623/17 |
| 6,296,664 B1 * | 10/2001 | Middleton ............ 623/17.15 |
| 6,375,655 B1 * | 4/2002 | Zdeblick et al. ............ 606/61 |

\* cited by examiner

ARTIFICIAL INTERVERTEBRAL DISC

This application is a divisional application of application Ser. No. 09/098,606, filed Jun. 17, 1998 now U.S. Pat. No. 6,296,664.

BACKGROUND

1. Field of the Disclosure

The present disclosure generally relates to apparatus and techniques for treatment of spinal disorders, and, in particular, relates to an artificial intervertebral prosthesis which restores both the height and shape of the intervertebral disc space following the removal of a damaged or diseased intervertebral disc while maintaining the natural biomechanics of the spinal motion segment.

2. Description of the Prior Art

The objective in inverterbral disc replacement is to provide a prosthetic disc that combines both stability to support the high loads of the patient's vertebrae and flexibility to provide the patient with sufficient mobility and proper spinal column load distribution. In attempting to strike this balance, generally, four basic types of artificial intervertebral discs for replacing a part or all of a removed disc have been developed, namely, elastomer discs, ball and socket discs, mechanical spring discs and hybrid discs. Elastomer discs typically include an elastomer cushion which is sandwiched between lower and upper rigid endplates. The elastomer discs are advantageous in that the elastomer cushion functions similar in mechanical behavior to the removed intervertebral disc tissue. However, a disadvantage of this disc type is that the elastomer cushion experiences long term in-vivo problems stemming from microcracking, which detracts from its usefulness as a replacement option. Furthermore, attachment of the flexible elastomer cushion to rigid endplates presents additional difficulties, Examples of elastomer discs are disclosed in U.S. Pat. No. 5,702,450 to Bisserie; U.S. Pat. No. 5,035,716 to Downey; U.S. Pat. No. 4,874,389 to Downey; and U.S. Pat. No. 4,863,477 to Monson.

Ball and socket discs typically incorporate two plate members having cooperating inner ball and socket portions which permit articulating motion of the members during movement of the spine. The ball and socket arrangement is adept in restoring "motion" of the spine, but, is poor in replicating the natural stiffness of the intervertebral disc. Dislocation and wear are other concerns with this disc type. Examples of ball and socket discs are disclosed in U.S. Pat. No. 5,507,816 to Bullivant and U.S. Pat. No. 5,258,031 to Salib et al.

Mechanical spring discs usually incorporate one or more coiled springs disposed between metal endplates. The coiled springs preferably define a cumulative spring constant sufficient to maintain the spaced arrangement of the adjacent vertebrae and to allow normal movement of the vertebrae during flexion and extension of the spring in any direction. Disadvantages of the mechanical spring disc types involve attachment of the coiled springs to the metal end plates and associated wear at the attachment points. Examples of mechanical spring discs are disclosed in U.S. Pat. No. 5,458,642 to Beer et al. and U.S. Pat. No. 4,309,777 to Patil.

The fourth type of artificial intervertebral disc, namely, the hybrid type incorporates two or more principles of any of the aforedescribed disc types. For example, one known hybrid disc arrangement includes a ball and socket set surrounded by an elastomer ring. This hybrid disc provides several advantages with respect to load carrying ability, but, is generally complex requiring a number of individual components. Furthermore, long term in vivo difficulties with the elastomer cushion remain a concern as well as wear of the ball and socket arrangement.

Figure 1:
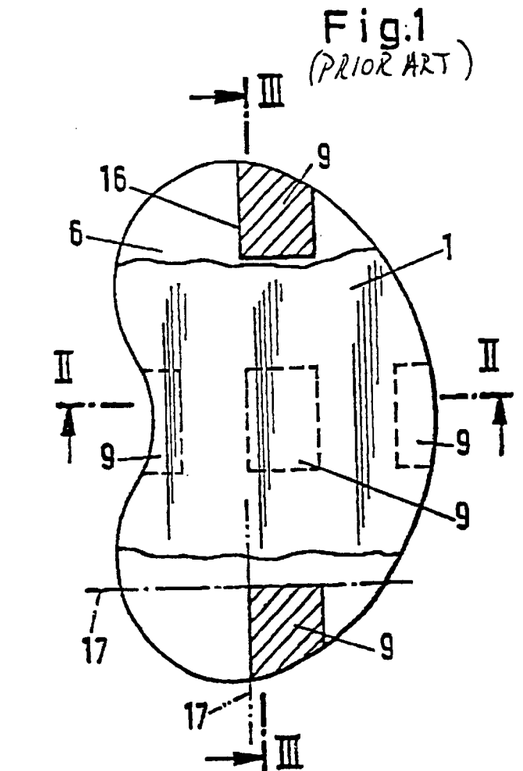
FIGS. 1–3 illustrate a prior art intervertebral disc prosthesis.
Figure 2:
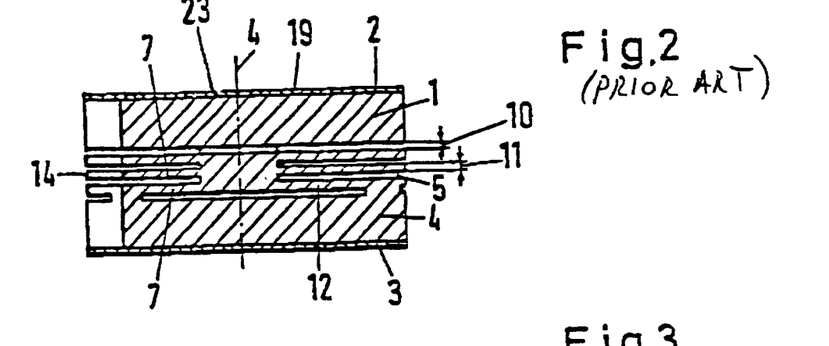
Figure 3:
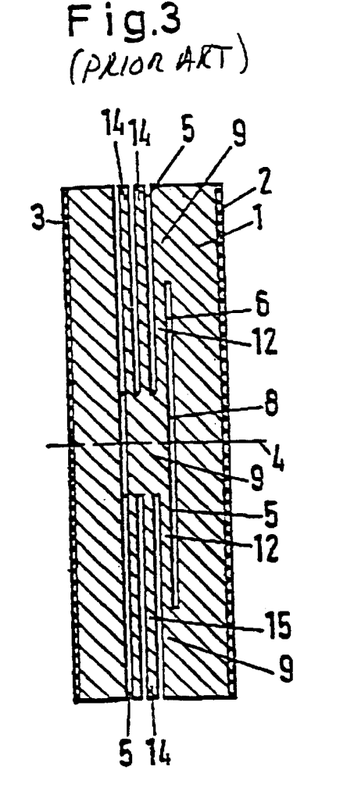

Another type of intervertebral disc prosthesis is disclosed in U.S. Pat. No. 5,320,644 to Baumgartner. With reference to FIGS. 1–3, the Baumgartner '644 device is a unitary intervertebral disc member 1 made from a strong, elastically deformable material. The disc member 1 has parallel slits 5 each arranged at a right angle to the axis of the disc member. The parallel slits 5 partially overlap one another to define overlapping regions 6 between adjacent slits. The overlapping regions 6 create leaf springs 7 for the transmission of forces from one vertebral attachment surface to the other. In regions of adjacent slits 5 where they do not overlap the spring action on the leaf springs 7 is interrupted by fixation zones 9 of solid prosthesis material. The forces acting on the intervertebral disc are transmitted from one leaf spring plane to the next leaf spring plane via the fixation zones 9.

However, the load paths are inherently abrupt with highly localized transfer of load through the sparsely placed fixation zones 9. There are even instances where the entire load is carried through a single fixation zone 9 in the center of the disc. The abrupt load paths can lead to high stress regions, which can detract from the appropriate biomechanical performance, i.e., strength, flexibility, and range-of-motion, of the prosthesis.

The need therefore exists for a prosthetic disc which is easy to manufacture and provides the proper balance of flexibility and stability through improved load distribution.

SUMMARY

Accordingly, the present disclosure is directed to an intervertebral disc prosthesis for insertion within the intervertebral space between adjacent vertebrae to replace at least a portion of an intervertebral disc removed therefrom. The intervertebral prosthesis includes a disc member having a longitudinal axis extending the height of the disc member and a radial axis transverse to the longitudinal axis. The disc member includes an external wall having at least one slit therein. The at least one slit has a first component of direction and a second different component of direction and facilitates transfer of load along the exterior wall.

Preferably, the exterior wall includes a plurality of helical slits, adjacent slits being disposed in radial relation with respect to the longitudinal axis whereby load transfer occurs along the exterior wall. The slits give the exterior wall flexibility consistent with the natural intervertebral disc.

The disc member may further include an inner cavity. Preferably, the slit(s) extends from an outer wall surface of the exterior wall to an inner wall surface thereof in communication with the inner cavity. First and second longitudinally opposed support surfaces are disposed at the longitudinal ends of the disc. The support surfaces are dimensioned to supportingly engage vertebral portions of respective vertebrae. At least one of the first and second support surfaces has an opening extending therethrough in communication with the inner cavity.

An end cap may be releasably mounted to the support surfaces and at least partially positionable within the opening in the support surface. The end cap may include an inner opening dimensioned to reduce rigidity thereof.

BRIEF DESCRIPTION OF THE DRAWINGS

Preferred embodiment(s) of the present disclosure are described herein with reference to the drawings wherein.

DETAILED DESCRIPTION OF THE PREFERRED EMBODIMENTS

Figure 4:
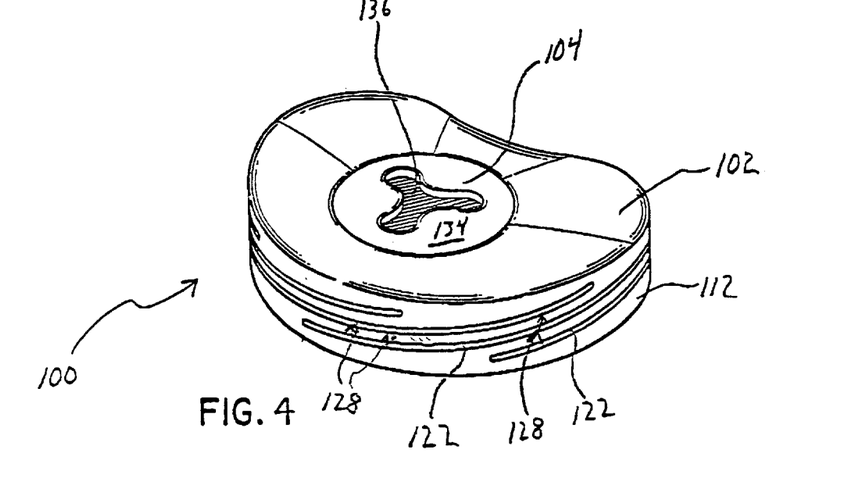
FIG. 4 is a perspective view of the artificial intervertebral prosthesis in accordance with the principles of the present disclosure, including the disc member and the end cap(s) mounted to the disc member.
Figure 5:
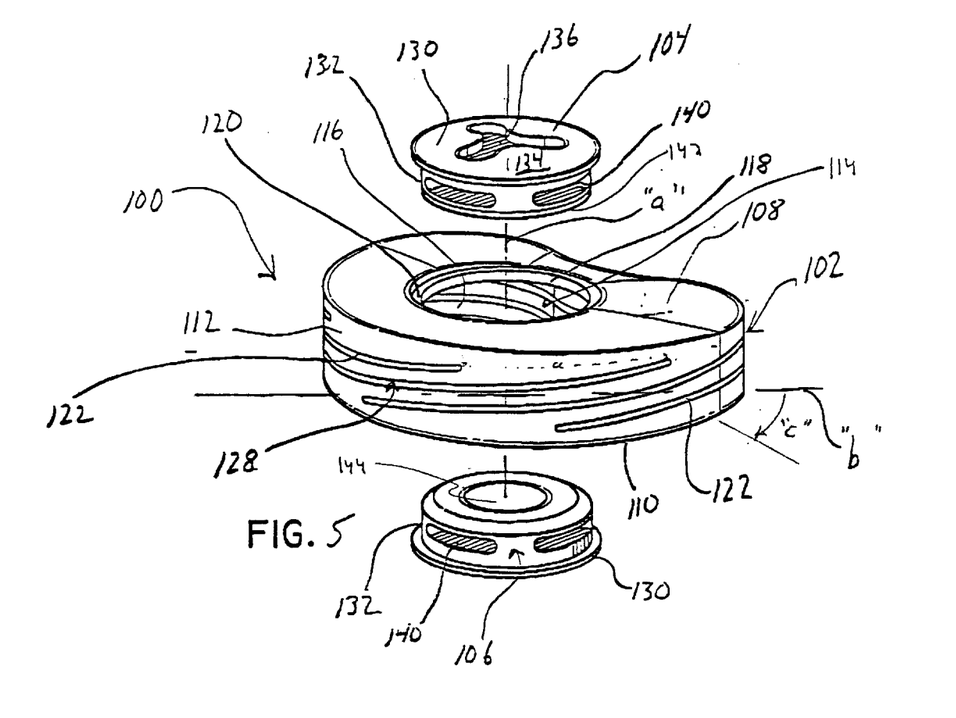
FIG. 5 is a perspective view of the intervertebral prosthesis of FIG. 4 with the end caps removed from the disc member.
Figure 6:
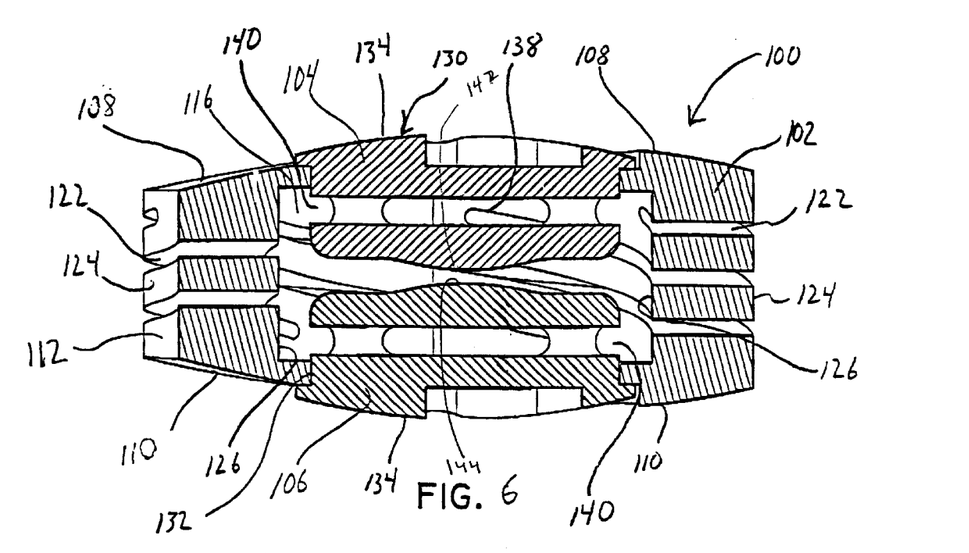
FIG. 6 is a cross-sectional view of the intervertebral prosthesis of FIG. 4.

Referring now to the drawings, in which like reference numerals identify similar or identical elements throughout the several views, and referring in particular to FIGS. 4–6, the artificial intervertebral prosthesis of the present disclosure is illustrated. Intervertebral prosthesis 100 is intended to replace part or all of the supporting function of a diseased intervertebral disc which had been previously removed through a discectomy procedure or the like. Intervertebral prosthesis 100 is advantageously dimensioned to be positioned between adjacent vertebrae in supporting contacting relation with the vertebral end plates thereof to maintain the adjacent vertebrae in appropriate spaced relation while restoring the natural biomechanics (e.g., including stiffness, range of motion, and strength) of the spinal or vertebral segment.

Intervertebral prosthesis 100 includes two basic components, namely, disc or body member 102 and first and second end caps 104, 106 which are releasably mounted to the body member 102. Body member 102 is in the general shape of an intervertebral disc (e.g., kidney-shaped) as shown and defines longitudinal axis "a" extending along the height of the member 102 and radial axis "b" generally transverse to the longitudinal axis "a". An angular reference is defined by "c" as shown. (FIG. 5) Body member 102 includes first and second longitudinally opposed (e.g., upper and lower) support surfaces 108, 110 which supportingly engage the respective end faces of the adjacent vertebrae upon insertion of the prosthesis, and exterior wall 112 extending between the support surfaces 108, 110. Support surfaces 108, 110 are each arcuate in configuration defining a slight outer curvature which preferably corresponds to the slight inward curvature of the vertebral end plates so as to facilitate positioning and retention of the prosthesis within the intervertebral space.

Body member 102 further includes a centrally located cannulation 116 in general alignment with the longitudinal axis "a" and extending through support members 108, 110. (FIG. 5) Cannulation or bore 116 defines an inner cavity 114 and central openings 118 of the support surfaces 108, 110. In the embodiment illustrated in FIG. 4, openings 118 are correspondingly dimensioned to at least partially receive their respective end caps 104, 106. An enlarged circumferential recess 120 is defined within each support surface 108, 110 about the periphery of each opening 118 to receive the head portion 130 on the end caps 104, 106. As shown, the end caps 104, 106 once inserted, are generally flush with the upper and lower surfaces 114. The end caps 104, 106 provide additional surfaces 134 for bone attachment and prevent bone growth into the body member 102. The engagement surfaces 142, 144 of the end caps 104, 106, during high load contact each other and serve several purposes: (1) prevent the exterior walls 112 from being overstressed by providing an alternate load path (through the center of the disc); (2) increase the overall stiffness of disc 100 in a similar manner as the natural disc which becomes more rigid with high loads; and (3) prevent complete closure of the generally helical slits 122, reducing a "pinching" effect on surrounding soft tissue. Internal bore 138 with its associate slotted openings 140 effectively reduce the rigidity of the end caps 104, 106, so that the overall stiffness of the disc 100 will be more consistent with the natural intervertebral disc.

With continued reference to FIGS. 4–6, exterior wall 112 has a plurality of slits 122 defined therein which, in the preferred embodiment, extend completely through the exterior wall from its outer surface 124 to its inner surface 126 in communication with the inner cavity 114. (FIG. 6) Each slit 122 is generally helical in configuration, i.e., each slit 122 has a longitudinal component of direction and an angular component of direction as shown. These different directional components e.g. a longitudinal and lateral direction, result in a multi-directional path for each of the slits 122. Slits 122 are preferably disposed about the exterior wall at predetermined spaced radial locations whereby adjacent longitudinal slits 122 are in partial overlapping arrangement. In the illustrated embodiment, five slits 122 are provided which are radially spaced at 72° intervals, although alternate numbers of slits and other spaced intervals are contemplated.

The slits 122 as shown extend to subtend an angle of about 180° around the exterior wall 112 relative to the longitudinal axis "a" although they can extend less than or greater than 180°. A single generally helical slit may be used, however, the preferred embodiment provides a plurality of generally helical slits 122. The helical slits 122 are disposed in a radial relation with respect to the radial axis "b" and angle "c". The remaining load path 128 of the device wall 112 has a spring-like characteristic, similar to a compressive or coiled spring. The plurality of load paths 128 create a flexible disc wall 112 and allow the transfer of loads between upper support surface 108 and lower support surface 110, in a continuous manner without abrupt load paths.

Although helical slits are shown, it is also contemplated that other multi-directional slits, i.e. having a lateral and longitudinal component of direction can be utilized. This can include slits that are smooth, piecewise smooth, open-looped, etc.

With further reference to FIGS. 4–6, end caps 104, 106 each define circumferential ledge or head portion 130 and main portion 132 of reduced dimension. End caps 104, 106 are at least partially received within central openings 118 of support surfaces 108, 110 in a manner whereby circumferential head portion 130 resides in correspondingly dimensioned circumferential recess 120 of the support surface 108, 110 and main portion 132 extends within the cannulation 116. The outer surface 134 of each end cap 104, 106 is preferably arcuate in shape generally corresponding to the arcuate configuration of the outer support surface 108, 110 to form a smooth transition from the outer support surfaces 108, 110 to the end cap. End caps 104, 106 each further include an indentation 136 defined in outer support surface 134 for attaching an instrument to releasably hold the end cap 104, 106 during insertion into the body member's 102 central openings 118. Indentation 136 is generally clover-shaped although other shapes are contemplated including rectangular, hexagonal, etc. to receive appropriate instrumentation. Main portion 132 of each end cap 104, 106 has a central internal bore or cavity 138 which extends through its outer wall to define a plurality (e.g., 4) of radially arranged slotted openings 140. Internal bore 138 with its associated radial openings 140 effectively reduce the rigidity of the respective end caps 104,106. The caps can alternatively have helical slits instead of openings 140 to further reduce stiffness.

The components of intervertebral prosthesis 100 are fabricated from a suitable rigid material including stainless steel, titanium or a suitable polymeric material. Preferably, the body member 102 is monolithically formed as a single unit although it is envisioned that in an alternate embodiment the body member 102 is composed of separate components, each of which would have the structural features, e.g. helical slit and inner cavity, discussed above. For example, three components can be utilized which when placed in juxtaposition in the invertebral space form the kidney shape of FIG. 4.

Insertion of the Artificial Intervertebral Disc

Figure 7:
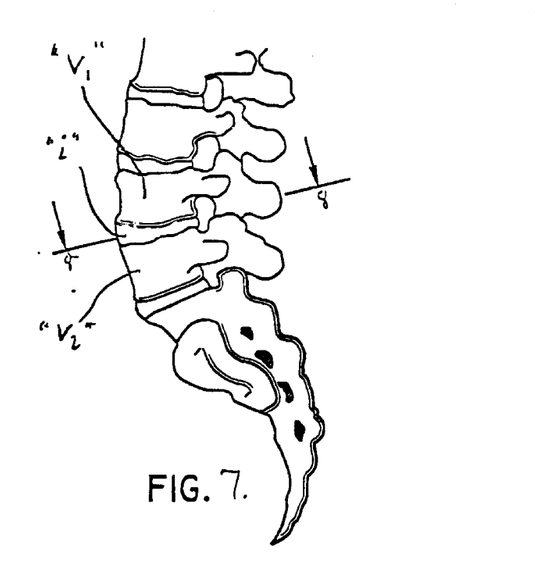
FIG. 7 is a view illustrating a portion of the vertebral column.
Figure 8:
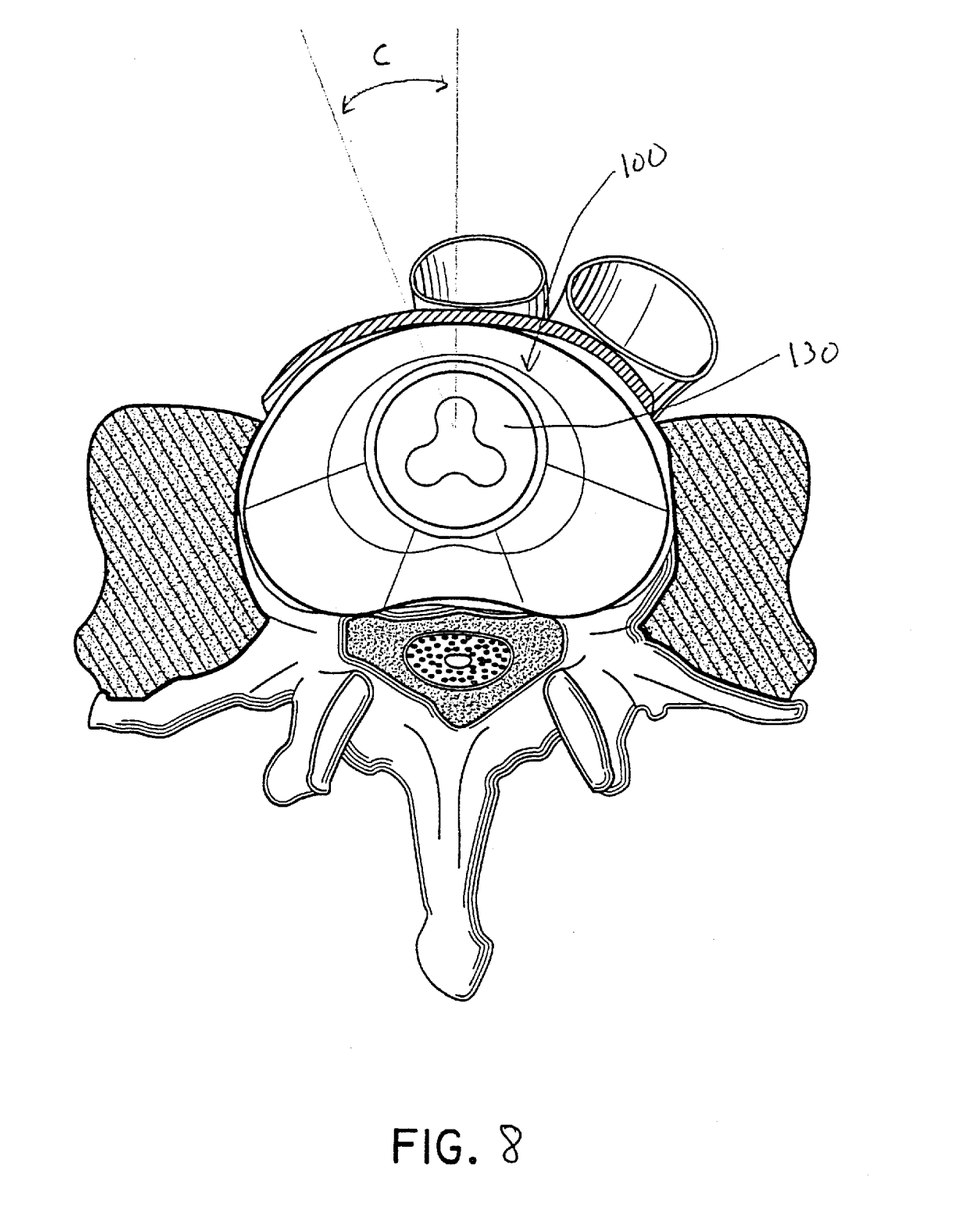
FIG. 8 is a view taken along the lines 8—8 of FIG. 7 illustrating the intervertebral prosthesis of FIG. 4 positioned within the intervertebral space defined between adjacent vertebrae.

With reference to FIGS. 7–8, the insertion of the artificial intervertebral disc will be discussed. The intervertebral space "i" defined between adjacent vertebrae "$V_1$, $V_2$" is accessed utilizing appropriate retractor instrumentation or the like. Thereafter, a partial or full discectomy is performed to remove the diseased portion of the disc. The adjacent vertebrae "$V_1$, $V_2$" are distracted with appropriate distractor instrumentation to expose the intervertebral space. The artificial intervertebral prosthesis 100 is then positioned within the intervertebral space "i". Upon placement, the upper and lower support surfaces 108, 110 engage the respective vertebral end plates of the adjacent vertebrae in supporting relation therewith. As noted above, the arcuate contours defined by the outer surfaces 134 of the end caps 104,106 and outer surfaces of the upper and lower support surfaces 108,110 approximates the arcuate contour of the vertebral end plates to snugly fit within the adjacent vertebrae and facilitate retention within the intervertebral space.

As indicated hereinabove, the artificial intervertebral prosthesis 100 is characterized by having sufficient rigidity to maintain the adjacent vertebrae in spaced relation while possessing adequate flexibility to permit flexural movement of the vertebral column. The loads applied to the intervertebral prosthesis 100 are transmitted between the upper and lower support surfaces 108, 110 through the exterior wall 112 along generally continuous paths via the helical slit 122 arrangement and the resulting plurality of load paths 128.

Alternate Embodiment(s)

Figure 9:
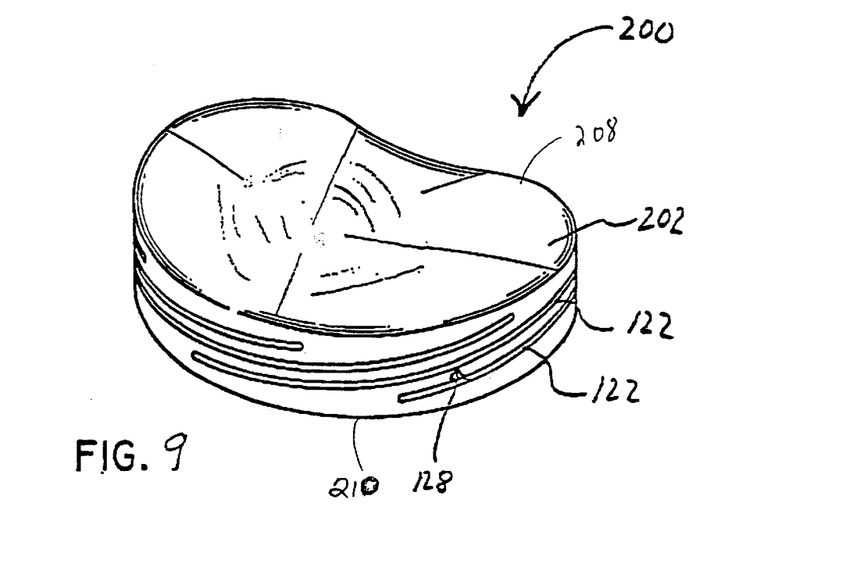
FIG. 9 is a perspective view of an alternate embodiment of the intervertebral disc prosthesis.

FIG. 9 illustrates an alternate embodiment of the present disclosure. Intervertebral prosthesis 200 includes disc or body member 202 which is substantially similar to body member 102 of the embodiment of FIG. 4. However, in accordance with this embodiment, end caps 104, 106 are eliminated such that the support surfaces 208, 210 are continuous. Also, there are no openings 118 within the support surfaces as in the embodiment of FIG. 4 (see surfaces 108, 110). The cavity or bore (not shown) extends internally between surfaces 208, 210. Thus, in accordance with this embodiment, the prosthesis is a single monolithically formed unit. Prosthesis 200 can include internal "caps" which contact each under heavy load to thereby function in a similar manner to the caps 104, 106 of prosthesis 100 of FIG. 4.

Figure 10:
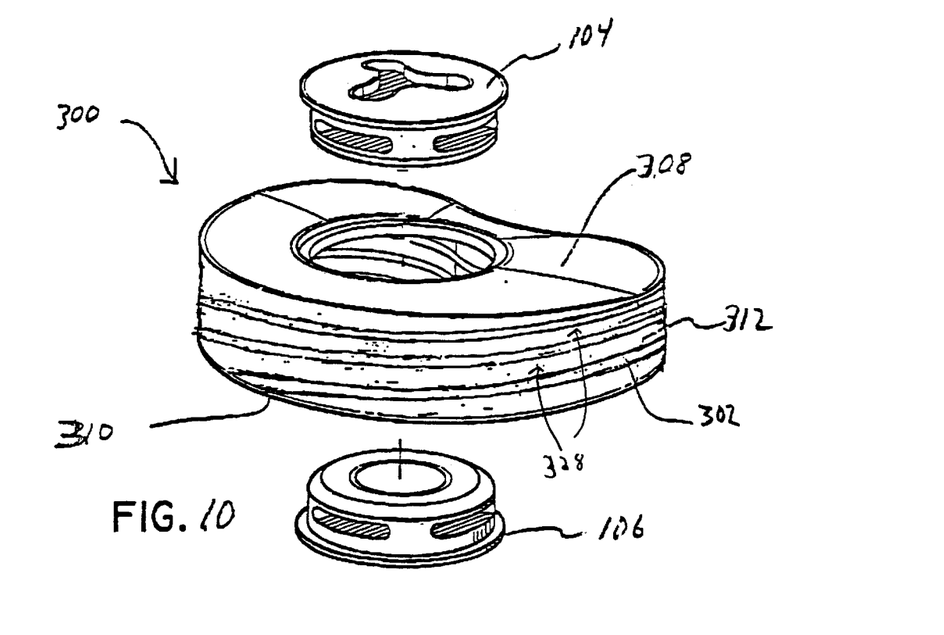
FIG. 10 is a perspective view of another alternate embodiment of the intervertebral disc prosthesis.

FIG. 10 illustrates another alternate embodiment of the present disclosure. Prosthesis 300 is substantially similar to prosthesis 100 of FIG. 4, however, in accordance with this embodiment, exterior wall 312 includes a single continuous helical slit 302 which extends from a position adjacent upper support surface 308 to a position adjacent lower support surface 310. The load paths are designated by reference numeral 328. This provides more flexibility. Continuous slit 302 defines overlapping regions wherein longitudinally displaced portions of the continuous slit are in partial overlapping relation. These overlapping regions of the continuous slit 302 also provide for a continuous load transfer from upper support surface 108 to lower support surface 110, the benefits of such arrangements being discussed hereinabove. End caps 104 and 106 can optionally be provided.

Fusion Cage with Helical Slit(s)

Figure 11A:
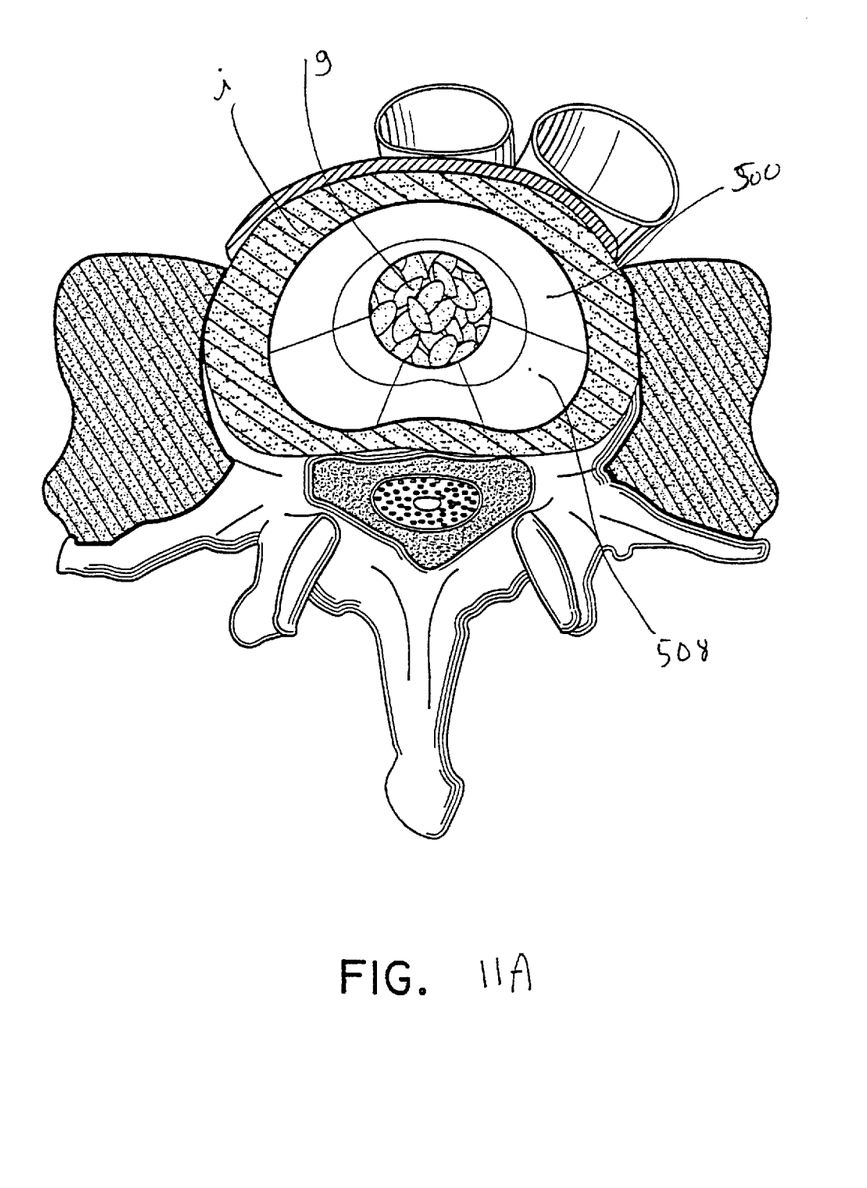
FIG. 11A is a cross-sectional view taken through the vertebral body to illustrate a top view of the fusion cage of the present disclosure.
Figure 11B:
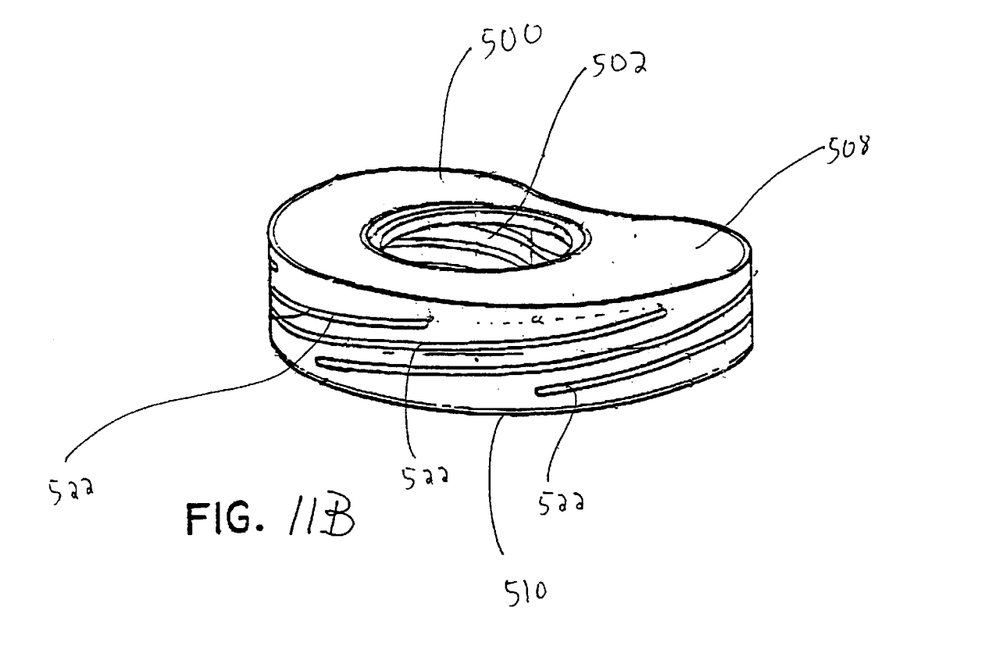
FIG. 11B is a perspective view of the fusion cage of FIG. 1A.

The present disclosure also includes a unique fusion cage illustrated in FIGS. 11A and 11B and designated generally by reference numeral 500. In the use of spinal fusion cages, load sharing with the bone graft packed within the cage is necessary to transform the bone graft into a solid bony arthrodesis. With current fusion cages, such as those made of titanium alloy, the cage is rigid, resulting in the cage as the dominant load path during the fusion process.

The fusion cage 500 of the present disclosure is preferably composed of a titanium alloy. However, the cage includes a slit configuration to reduce stiffness. That is, the helical slits 522 provide the cage with additional flexibility so they flex under load, resulting in greater load sharing with the graft. As can be appreciated, fusion cage 500 has the identical helical slit configuration as the prosthetic disc of FIG. 4, and therefore the slit configuration will not be described again. Note that the slit design of FIG. 10 can also be utilized.

Cage 500 includes an internal cavity 502 to receive bone graft material "g" (see FIG. 11A). End caps (not shown) can be provided to help retain the bone graft material and to limit flexure as described above, as long as the caps have openings communicating with the internal cavity 502 to ensure contact between the bone graft material and vertebrae. Once the cage 500 is placed in the vertebral space "i" with support surfaces 508, 510 contacting the vertebrae, this bone graft material inside cavity 502 fuses with the adjacent vertebrae over time. As shown in FIG. 11A, as with current fusion cages, cage 500 is smaller than the overall disc space. Although one is shown, it is contemplated that two or more cages 500 can be placed side by side in the disc space.

Also, since fusion cage 500 does not fill the entire disc space, shapes other than the kidney shape of FIGS. 11A and 11B are also contemplated, provided they contain the slit configuration to reduce overall flexibility It will be understood that various modifications may be made to the embodiment disclosed herein. Therefore, the above description should not be construed as limiting but merely as an exemplification of a preferred embodiment. Those skilled in the art will envision other modifications within the scope and spirit of the claims appended hereto.

What is claimed is:

1. An intervertebral implant which comprises:

a spacer member dimensioned for positioning within adjacent vertebrae to support the vertebrae in spaced relation, the spacer member including an exterior wall defining an internal cavity and having first and second end surfaces, at least one of the end surfaces defining an opening in communication with the internal cavity; and an end cap positionable within the opening in the one end surface, the end cap including a longitudinally extending outer wall extending from said one end surface into the internal cavity, the outer wall having wall surface portions defining a slot therein extending through said outer wall in a circumferential direction to reduce rigidity of the end cap.

2. The intervertebral prosthesis according to claim 1 wherein the spacer member defines a longitudinal axis whereby the first and second end surfaces are axial and surfaces for positioning adjacent respective vertebral portions of the adjacent vertebrae in contacting relation therewith.

3. The intervertebral prosthesis according to claim 2 wherein the outer wall of the end cap defines an inner cavity, the slot of the outer wall extending to the inner cavity.

4. The intervertebral prosthesis according to claim 3 wherein the outer wall of the end cap includes a plurality of slots equidistally disposed about the outer wall.

5. The intervertebral prosthesis according to claim 1 wherein the exterior wall of the spacer includes wall surface portions defining a helical slit therein and being dimensioned to permit the exterior wall to elastically deform when subjected to a load.

* * * * *

UNITED STATES PATENT AND TRADEMARK OFFICE
CERTIFICATE OF CORRECTION

PATENT NO. : 6,656,224 B2
DATED : December 2, 2003
INVENTOR(S) : Lance Middleton It is certified that error appears in the above-identified patent and that said Letters Patent is hereby corrected as shown below:

<u>Column 1,</u>
Line 2, insert -- CROSS REFERENCE TO RELATED APPLICATIONS --.

<u>Column 3,</u>
Line 27, "1A" should read -- 11A --.

Signed and Sealed this

Tenth Day of February, 2004

JON W. DUDAS
*Acting Director of the United States Patent and Trademark Office*